(12) United States Patent
Newman et al.

(10) Patent No.: US 12,016,756 B2
(45) Date of Patent: Jun. 25, 2024

(54) ULTRATHIN ABSORBENT HYGIENIC PADS

(71) Applicant: LYV Life, Inc., San Francisco, CA (US)

(72) Inventors: Morgen Newman, San Francisco, CA (US); Molly Hayward, San Francisco, CA (US)

(73) Assignee: LYV Life, Inc., San Francisco, CA (US)

(*) Notice: Subject to any disclaimer, the term of this patent is extended or adjusted under 35 U.S.C. 154(b) by 956 days.

(21) Appl. No.: 16/955,016

(22) PCT Filed: Dec. 18, 2018

(86) PCT No.: PCT/US2018/066316
§ 371 (c)(1),
(2) Date: Jun. 17, 2020

(87) PCT Pub. No.: WO2019/126226
PCT Pub. Date: Jun. 27, 2019

(65) Prior Publication Data
US 2020/0375811 A1 Dec. 3, 2020

Related U.S. Application Data

(60) Provisional application No. 62/607,884, filed on Dec. 19, 2017.

(30) Foreign Application Priority Data

Dec. 22, 2017 (EP) .................... 17382893

(51) Int. Cl.
*A61F 13/15* (2006.01)
*A61F 13/472* (2006.01)
(Continued)

(52) U.S. Cl.
CPC ...... *A61F 13/472* (2013.01); *A61F 13/51108* (2013.01); *A61F 13/532* (2013.01);
(Continued)

(58) Field of Classification Search
CPC .............. A61F 13/472; A61F 13/51108; A61F 13/532; A61F 13/5514; A61F 13/47;
(Continued)

(56) References Cited

U.S. PATENT DOCUMENTS 1,777,855 A 10/1930 Frank et al.
3,181,410 A 5/1965 Phillips
(Continued)

FOREIGN PATENT DOCUMENTS

CN 201822974 U 5/2011
CN 105559976 A 5/2016
(Continued)

OTHER PUBLICATIONS

Design U.S. Appl. No. 29/682,145 Office Action dated Dec. 31, 2020.
(Continued)

*Primary Examiner* — Jacqueline F Stephens
(74) *Attorney, Agent, or Firm* — J. Peter Paredes; Amin Wasserman Gurnani LLP

(57) ABSTRACT

Ultrathin absorbent hygienic pads comprising a top layer, a middle absorbent layer, and a bottom layer and comprising one or more channels anchored from the top layer through the middle absorbent layer and into the bottom layer are provided. The ultrathin absorbent hygienic pads provided can be used to absorb bodily fluids.

15 Claims, 8 Drawing Sheets

(51) Int. Cl.
*A61F 13/511* (2006.01)
*A61F 13/532* (2006.01)
*A61F 13/551* (2006.01)
A61F 13/53 (2006.01)
A61F 13/539 (2006.01)

(52) U.S. Cl.
CPC ..... *A61F 13/5514* (2013.01); *A61F 13/51113* (2013.01); *A61F 2013/530481* (2013.01); *A61F 2013/53908* (2013.01); *A61F 2013/53991* (2013.01)

(58) Field of Classification Search
CPC ........ A61F 13/49; A61F 13/53; A61F 13/535; A61F 13/536; A61F 13/4756; A61F 13/4704; A61F 2013/53908; A61F 2013/530481; A61F 2013/530175
See application file for complete search history.

(56) References Cited

U.S. PATENT DOCUMENTS

| | | |
|---|---|---|
| 3,404,682 A | 10/1968 | Waldron |
| 3,664,040 A | 5/1972 | Ouimet |
| 4,253,372 A | 3/1981 | Filipetti |
| D260,529 S | 9/1981 | Pearse |
| 4,347,773 A | 9/1982 | Zook |
| D310,233 S | 8/1990 | Farnell, Jr. |
| 4,950,264 A * | 8/1990 | Osborn, III ....... A61F 13/15203 604/385.08 |
| D317,171 S | 5/1991 | Saks |
| D323,212 S | 1/1992 | Crawford |
| D351,719 S | 10/1994 | Piotrowicz |
| D354,349 S | 1/1995 | Grein |
| 5,397,316 A | 3/1995 | Lavon et al. |
| D368,519 S | 4/1996 | Harrison et al. |
| 5,520,674 A | 5/1996 | Lavon et al. |
| H1657 H | 6/1997 | Hammons et al. |
| 5,676,652 A | 10/1997 | Hunter et al. |
| 5,704,929 A | 1/1998 | Bien |
| D393,712 S | 4/1998 | Clay |
| H1746 H | 8/1998 | Carrier et al. |
| D427,728 S | 7/2000 | Ferguson |
| D431,293 S | 9/2000 | Finkle et al. |
| D432,234 S | 10/2000 | Schlinz et al. |
| 6,160,197 A | 12/2000 | Lassen et al. |
| D440,307 S | 4/2001 | Richardson et al. |
| D440,315 S | 4/2001 | Hassenbein et al. |
| D440,655 S | 4/2001 | Richardson et al. |
| D440,656 S | 4/2001 | Richardson et al. |
| D443,928 S | 6/2001 | Richardson et al. |
| D444,231 S | 6/2001 | Renz et al. |
| D446,301 S | 8/2001 | Schlinz et al. |
| D446,913 S | 8/2001 | Holden |
| 6,319,239 B1 | 11/2001 | Daniels et al. |
| D454,195 S | 3/2002 | Kitzinger et al. |
| D455,002 S | 4/2002 | Holden |
| D461,242 S | 8/2002 | Brisebois et al. |
| D461,893 S | 8/2002 | Gannon et al. |
| D463,547 S | 9/2002 | Mascuilli |
| D463,549 S | 9/2002 | Gannon et al. |
| 6,475,199 B1 | 11/2002 | Gann et al. |
| 6,520,945 B1 | 2/2003 | Hansson |
| D472,629 S | 4/2003 | Edens et al. |
| D473,642 S | 4/2003 | De Carvalho et al. |
| 6,551,296 B1 | 4/2003 | Boulanger |
| D474,272 S | 5/2003 | Boser |
| 6,563,013 B1 | 5/2003 | Murota |
| D476,739 S | 7/2003 | De Carvalho et al. |
| D478,985 S | 8/2003 | De Carvalho et al. |
| D482,781 S | 11/2003 | Glaug et al. |
| D482,782 S | 11/2003 | Glaug et al. |
| D482,783 S | 11/2003 | Glaug et al. |
| D482,824 S | 11/2003 | Robinson |
| D483,117 S | 12/2003 | Glaug et al. |
| D483,118 S | 12/2003 | Glaug et al. |
| D483,119 S | 12/2003 | Glaug et al. |
| D486,228 S | 2/2004 | Fonseca et al. |
| D489,451 S | 5/2004 | Glaug et al. |
| D489,821 S | 5/2004 | Glaug et al. |
| D490,892 S | 6/2004 | Schlueter et al. |
| D495,419 S | 8/2004 | Dunshee |
| D498,841 S | 11/2004 | Bell et al. |
| D500,176 S | 12/2004 | Watson |
| D503,977 S | 4/2005 | Bierman |
| 6,908,456 B1 | 6/2005 | Drevik |
| 6,911,574 B1 | 6/2005 | Mizutani |
| D509,024 S | 8/2005 | Pimentel |
| 6,951,046 B2 | 10/2005 | Robinson |
| D511,573 S | 11/2005 | Mueller et al. |
| D516,727 S | 3/2006 | Neri |
| D519,239 S | 4/2006 | Katagiri |
| D523,957 S | 6/2006 | Persson |
| 7,087,806 B2 | 8/2006 | Scheinberg et al. |
| D527,824 S | 9/2006 | Mueller et al. |
| D528,656 S | 9/2006 | Glaug et al. |
| 7,195,619 B2 | 3/2007 | Manasek |
| D551,041 S | 9/2007 | Park |
| D553,243 S | 10/2007 | Bader |
| D554,254 S | 10/2007 | Cole |
| 7,278,988 B2 | 10/2007 | Molas et al. |
| 7,291,136 B1 | 11/2007 | Drevik et al. |
| D570,488 S | 6/2008 | Kirksey et al. |
| D571,004 S | 6/2008 | Cardin et al. |
| D574,078 S | 7/2008 | Larson et al. |
| D574,085 S | 7/2008 | Lucchetti |
| D576,282 S | 9/2008 | Yanaki |
| D577,442 S | 9/2008 | Reed et al. |
| D577,884 S | 10/2008 | Swilley, Sr. |
| D578,212 S | 10/2008 | Perkins |
| D580,639 S | 11/2008 | Wurzburg |
| D580,640 S | 11/2008 | Wurzburg |
| D583,103 S | 12/2008 | Holden |
| D585,095 S | 1/2009 | Crosby et al. |
| D585,984 S | 2/2009 | Cardin et al. |
| D587,271 S | 2/2009 | Johnson et al. |
| D592,743 S | 5/2009 | Moennig |
| D593,682 S | 6/2009 | Freeland |
| D594,972 S | 6/2009 | Cauwood et al. |
| D594,977 S | 6/2009 | Jackson et al. |
| D595,844 S | 7/2009 | Giloh |
| D607,112 S | 12/2009 | Rogers et al. |
| D607,113 S | 12/2009 | Rogers et al. |
| D607,194 S | 1/2010 | Zagula |
| D608,887 S | 1/2010 | Kyvik et al. |
| D609,359 S | 2/2010 | Yim |
| D611,243 S | 3/2010 | Weisser |
| D612,491 S | 3/2010 | Sullivan Conrad et al. |
| D618,357 S | 6/2010 | Navies |
| D621,501 S | 8/2010 | Coon |
| D631,151 S | 1/2011 | Lundstrom et al. |
| D632,020 S | 2/2011 | Onrot et al. |
| D636,487 S | 4/2011 | Nnenna Idima Igwe |
| D642,267 S | 7/2011 | Dragan |
| D645,675 S | 9/2011 | Rice et al. |
| D646,382 S | 10/2011 | Connor |
| D647,200 S | 10/2011 | Slaughter |
| D648,849 S | 11/2011 | Houle |
| D651,306 S | 12/2011 | Misiti et al. |
| D654,532 S | 2/2012 | Morales |
| D655,076 S | 3/2012 | Rosenberg |
| D662,587 S | 6/2012 | Fernandez |
| 8,197,844 B2 | 6/2012 | Yanaki |
| D663,931 S | 7/2012 | Allen et al. |
| D668,332 S | 10/2012 | Hough et al. |
| D672,035 S | 12/2012 | Paques et al. |
| D674,587 S | 1/2013 | Grainger |
| D688,017 S | 8/2013 | Uchiyama et al. |
| D692,056 S | 10/2013 | Wolk et al. |
| D692,137 S | 10/2013 | Sicurelli |
| D692,565 S | 10/2013 | Lattimore et al. |
| D704,827 S | 5/2014 | Hood et al. |
| D705,442 S | 5/2014 | Tipton et al. |
| D710,629 S | 8/2014 | Franco |

(56) References Cited

U.S. PATENT DOCUMENTS

| | | |
|---|---|---|
| D712,549 S | 9/2014 | Igwebuike et al. |
| D714,406 S | 9/2014 | Saruma |
| D715,923 S | 10/2014 | Cardin et al. |
| D716,584 S | 11/2014 | Franco |
| D716,866 S | 11/2014 | Chappo et al. |
| D716,938 S | 11/2014 | Fitter et al. |
| D721,181 S | 1/2015 | Schiebl |
| D723,176 S | 2/2015 | Igwebuike et al. |
| D723,702 S | 3/2015 | Igwebuike et al. |
| D729,391 S | 5/2015 | Igwebuike et al. |
| D731,644 S | 6/2015 | Robles et al. |
| D733,311 S | 6/2015 | Takanishi et al. |
| D736,085 S | 8/2015 | Markle et al. |
| D736,909 S | 8/2015 | Labit et al. |
| D738,493 S | 9/2015 | Cardin et al. |
| D739,015 S | 9/2015 | Martin |
| D739,531 S | 9/2015 | Sicurelli |
| D744,093 S | 11/2015 | Bova et al. |
| 9,173,783 B1 | 11/2015 | Terian et al. |
| D746,480 S | 12/2015 | Usui |
| 9,220,645 B2 | 12/2015 | Babusik et al. |
| D747,467 S | 1/2016 | Green |
| D749,720 S | 2/2016 | Hedbratt et al. |
| D752,327 S | 3/2016 | Yoon |
| D752,764 S | 3/2016 | Peters |
| D759,828 S | 6/2016 | Riedle |
| D760,991 S | 7/2016 | Ajmera et al. |
| D762,053 S | 7/2016 | Takahashi |
| D764,675 S | 8/2016 | Peisner et al. |
| D766,427 S | 9/2016 | Kurov et al. |
| D768,360 S | 10/2016 | Jones |
| D768,370 S | 10/2016 | Kanji et al. |
| D768,963 S | 10/2016 | Amrikhas et al. |
| D771,246 S | 11/2016 | Raycheck et al. |
| D771,363 S | 11/2016 | Vasyli |
| D771,912 S | 11/2016 | Mirkovic et al. |
| D773,040 S | 11/2016 | Fites et al. |
| 9,504,613 B2 | 11/2016 | Geilich et al. |
| D774,202 S | 12/2016 | Bielitz |
| D774,642 S | 12/2016 | Stahl |
| D775,802 S | 1/2017 | Takahashi |
| D776,769 S | 1/2017 | Heath |
| D777,911 S | 1/2017 | Niemeyer et al. |
| D780,483 S | 3/2017 | Della Santina |
| D780,915 S | 3/2017 | Castillo |
| D783,811 S | 4/2017 | Plumley |
| D783,841 S | 4/2017 | Riesinger |
| D787,688 S | 5/2017 | Stephenson |
| D787,689 S | 5/2017 | Roberts |
| D789,524 S | 6/2017 | Fites et al. |
| D789,525 S | 6/2017 | Fites et al. |
| D790,689 S | 6/2017 | Noel |
| D794,180 S | 8/2017 | Frisk |
| D796,031 S | 8/2017 | Robles et al. |
| D797,473 S | 9/2017 | Wilkinson et al. |
| D798,397 S | 9/2017 | Bellevue |
| D798,442 S | 9/2017 | Fites et al. |
| D798,462 S | 9/2017 | Sengelmann |
| 9,820,897 B2 | 11/2017 | Berry |
| D804,658 S | 12/2017 | Fites et al. |
| D806,865 S | 1/2018 | Stahl |
| D809,653 S | 2/2018 | Kremer |
| D811,610 S | 2/2018 | Abel et al. |
| D811,611 S | 2/2018 | Lind et al. |
| D811,615 S | 2/2018 | Lind et al. |
| D815,289 S | 4/2018 | Evers et al. |
| D818,578 S | 5/2018 | Stahl |
| D820,975 S | 6/2018 | Gressle |
| D826,151 S | 8/2018 | Akana et al. |
| D827,061 S | 8/2018 | Trenkle |
| D829,324 S | 9/2018 | Fitter et al. |
| D829,376 S | 9/2018 | Howard et al. |
| D832,438 S | 10/2018 | Brockway |
| D834,201 S | 11/2018 | Heinecke et al. |
| D836,196 S | 12/2018 | Ahn |
| 10,182,616 B2 | 1/2019 | O'Brien |
| D840,721 S | 2/2019 | Amrine et al. |
| D840,722 S | 2/2019 | Amrine et al. |
| D841,233 S | 2/2019 | Tai |
| D841,359 S | 2/2019 | Crevier |
| D841,808 S | 2/2019 | Drach |
| D841,968 S | 3/2019 | Toms, Jr. et al. |
| D842,599 S | 3/2019 | Toms, Jr. et al. |
| D844,779 S | 4/2019 | Pinion |
| D848,004 S | 5/2019 | Del Rossi et al. |
| D852,411 S | 6/2019 | Grund et al. |
| D855,191 S | 7/2019 | Hong et al. |
| D855,884 S | 8/2019 | Batchvarova et al. |
| D856,596 S | 8/2019 | Conway |
| D857,884 S | 8/2019 | Hood et al. |
| 10,418,004 B1 | 9/2019 | Tomasi et al. |
| D861,777 S | 10/2019 | Hunter |
| D862,599 S | 10/2019 | Marcinkowski |
| D863,562 S | 10/2019 | Hahn |
| D866,655 S | 11/2019 | Vanmeter |
| D866,656 S | 11/2019 | Vanmeter |
| D866,770 S | 11/2019 | Hahn et al. |
| D869,652 S | 12/2019 | Berken et al. |
| D869,834 S | 12/2019 | Kim |
| D870,276 S | 12/2019 | Berken et al. |
| D874,069 S | 1/2020 | Dunton |
| D875,958 S | 2/2020 | Emslander et al. |
| D876,640 S | 2/2020 | King |
| D879,955 S | 3/2020 | Fitter et al. |
| D880,062 S | 3/2020 | Seguinot |
| 10,607,581 B1 | 3/2020 | Johnson |
| D882,073 S | 4/2020 | Bremer et al. |
| D882,074 S | 4/2020 | Berken et al. |
| D882,771 S | 4/2020 | Hedbratt |
| D882,773 S | 4/2020 | Vandenboogart et al. |
| D882,776 S | 4/2020 | Berken et al. |
| D882,907 S | 5/2020 | Dale |
| D886,227 S | 6/2020 | Rofkahr, Jr. et al. |
| D886,371 S | 6/2020 | Oh |
| D888,256 S | 6/2020 | Del Rossi et al. |
| D888,406 S | 6/2020 | Goldman |
| 10,667,597 B2 | 6/2020 | Chaillet-Piquand et al. |
| D889,671 S | 7/2020 | Kase et al. |
| D891,625 S | 7/2020 | Sharkus |
| D892,732 S | 8/2020 | Akana et al. |
| D892,908 S | 8/2020 | Downing |
| D893,022 S | 8/2020 | Bremer et al. |
| D894,529 S | 9/2020 | Henderson |
| D897,526 S | 9/2020 | Fites et al. |
| D901,698 S | 11/2020 | Dyer et al. |
| 2001/0009992 A1 | 7/2001 | Boulanger et al. |
| 2002/0072725 A1 | 6/2002 | Kolby-Falk |
| 2002/0128622 A1 | 9/2002 | Carvalho et al. |
| 2003/0125701 A1 | 7/2003 | Widlund |
| 2003/0153890 A1 | 8/2003 | Rosenfeld |
| 2003/0225383 A1 | 12/2003 | Glaug et al. |
| 2003/0225385 A1 | 12/2003 | Glaug et al. |
| 2005/0124960 A1 | 6/2005 | Ruman |
| 2006/0058761 A1 | 3/2006 | Kudo et al. |
| 2007/0073255 A1* | 3/2007 | Thomas ............... A61F 13/8405 604/385.02 |
| 2007/0135787 A1 | 6/2007 | Raidel et al. |
| 2008/0103468 A1 | 5/2008 | Elfsberg et al. |
| 2008/0160856 A1 | 7/2008 | Chen et al. |
| 2008/0183150 A1 | 7/2008 | Nanjyo et al. |
| 2008/0269707 A1 | 10/2008 | Song |
| 2009/0036854 A1 | 2/2009 | Guidotti et al. |
| 2009/0112173 A1 | 4/2009 | Bissah et al. |
| 2009/0306614 A1 | 12/2009 | Boissier |
| 2010/0076389 A1 | 3/2010 | Burrow et al. |
| 2010/0268185 A1 | 10/2010 | Bergstrom et al. |
| 2010/0280474 A1 | 11/2010 | Bruzadin et al. |
| 2010/0324518 A1 | 12/2010 | Naoto et al. |
| 2010/0331804 A1 | 12/2010 | Larsson |
| 2011/0092944 A1 | 4/2011 | Sagisaka et al. |
| 2012/0260788 A1 | 10/2012 | Leneman |
| 2013/0092008 A1 | 4/2013 | Murphy |
| 2013/0261586 A1 | 10/2013 | Lee et al. |
| 2013/0274701 A1 | 10/2013 | Hayashi et al. |

(56) References Cited

U.S. PATENT DOCUMENTS

| | | |
|---|---|---|
| 2013/0345656 A1 | 12/2013 | Kato et al. |
| 2014/0066876 A1 | 3/2014 | Johansson |
| 2014/0090540 A1 | 4/2014 | Panagiotes |
| 2014/0128828 A1 | 5/2014 | Andersson et al. |
| 2014/0228796 A1 | 8/2014 | Burvall et al. |
| 2014/0243771 A1 | 8/2014 | Konishi et al. |
| 2015/0032073 A1 | 1/2015 | Noda et al. |
| 2015/0051566 A1 | 2/2015 | Noda et al. |
| 2015/0080837 A1* | 3/2015 | Rosati ............ A61F 13/45 604/385.101 |
| 2015/0272787 A1 | 10/2015 | Seitz et al. |
| 2015/0328061 A1 | 11/2015 | Bagger-Sjoback |
| 2015/0328063 A1 | 11/2015 | Esping et al. |
| 2015/0342795 A1 | 12/2015 | Alzate Machado et al. |
| 2016/0180824 A1 | 6/2016 | Mearini |
| 2016/0296385 A1 | 10/2016 | Samuelsson |
| 2016/0310330 A1 | 10/2016 | Knos et al. |
| 2017/0103737 A1 | 4/2017 | Hierholzer |
| 2017/0124992 A1 | 5/2017 | Cobb |
| 2017/0128284 A1 | 5/2017 | Esping et al. |
| 2018/0247619 A1 | 8/2018 | Hierholzer |
| 2018/0303680 A1 | 10/2018 | Hood et al. |
| 2019/0099301 A1 | 4/2019 | Viens et al. |
| 2019/0159946 A1 | 5/2019 | Descheemaecker et al. |
| 2019/0350773 A1 | 11/2019 | Biasutti et al. |
| 2019/0350775 A1 | 11/2019 | Biasutti et al. |
| 2020/0342834 A1 | 10/2020 | Choi |

FOREIGN PATENT DOCUMENTS

| | | | |
|---|---|---|---|
| EP | 1834019 A1 * | 9/2007 | ........... A61F 13/514 |
| JP | 2017093950 A | 6/2017 | |
| WO | WO-2019126226 A1 | 6/2019 | |
| WO | WO-2020190955 A1 | 9/2020 | |

OTHER PUBLICATIONS

Co-pending U.S. Appl. No. 29/682,142, filed Mar. 1, 2019.
Co-pending U.S. Appl. No. 29/682,143, filed Mar. 1, 2019.
Co-pending U.S. Appl. No. 29/682,145, filed Mar. 1, 2019.
Co-pending U.S. Appl. No. 29/682,148, filed Mar. 1, 2019.
Co-pending U.S. Appl. No. 29/682,149, filed Mar. 1, 2019.
PCT/US2018/066316 International Search Report and Written Opinion dated Mar. 14, 2019.
PCT/US2020/023175 International Search Report and Written Opinion dated Jun. 12, 2020.
Design U.S. Appl. No. 29/682,148 Office Action dated Mar. 6, 2020.
Design U.S. Appl. No. 29/682,149 Office Action dated Mar. 6, 2020.

* cited by examiner

ULTRATHIN ABSORBENT HYGIENIC PADS

CROSS-REFERENCE TO RELATED APPLICATIONS

This application claims the benefit of U.S. Provisional Patent Application No. 62/607,884, filed on Dec. 19, 2017 pursuant to 35 U.S.C. § 119. The above noted patent application is incorporated by reference as if set forth fully herein.

BACKGROUND

Ultrathin highly absorbent articles are essential products for people throughout the world, including products for urine and menstrual discharge. Absorbent articles must balance the ability to absorb and store fluid with a size and shape that is not uncomfortable or irritating. Many ultrathin absorbent articles utilize wicking materials that draw fluid away from the skin of the wearer and direct the fluid to an absorbent layer where the fluid is absorbed and stored. Unfortunately, many absorbent articles do not operate with the desired efficiency and effectiveness because some of the fluid may fail to be absorbed when the absorbent article has reached its maximum absorption and storage capacity or some of the fluid may leak before the entirety of the absorbent article has come into contact with the fluid. This can especially be a problem for absorbent articles that become saturated at the point of insult (the point where the fluid is introduced to the absorbent article), such as the center of a menstrual pad, which can become supersaturated and cause additional fluid to leak off the sides of the absorbent article even though the front portion and back portion of the absorbent article are untouched by fluid. To counter the problem of an inability to distribute fluid across the entirety of an absorbent article, many manufacturers have made thicker absorbent articles in order to accommodate the supersaturation that can occur at the center of the pad. However, thicker absorbent articles are less desirable from a comfort and a convenience standpoint. As such, there remains a need for an ultrathin absorbent article with improved efficiency and effectiveness for absorbing fluids.

SUMMARY

In some embodiments, disclosed herein are absorbent articles comprising a top layer, a middle absorbent layer, and a bottom layer, wherein the top layer comprises one or more channels anchored from the top layer through the middle absorbent layer and into the bottom layer. In some embodiments, the absorbent articles disclosed herein comprise one or more channels anchored via ultrasonic welding from the top layer through the middle absorbent layer and into the bottom layer. In some embodiments, the absorbent articles disclosed herein comprise two or more channels anchored from the top layer through the middle absorbent layer and into the bottom layer. In some embodiments, the absorbent articles disclosed herein comprise a top layer, a middle absorbent layer, and a bottom layer, wherein the top layer and the middle absorbent layer are bonded together with an adhesive. In some embodiments, the absorbent articles disclosed herein comprise a top layer comprising a non-woven spun sheet bound to an aperture layer. In some embodiments, the absorbent articles disclosed herein comprise a top layer comprising a non-woven spun sheet bound to an aperture layer wherein the aperture layer comprises a plurality of holes. In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the middle absorbent layer comprises a fluid drawing material and a fluid storage material. In some embodiments, disclosed herein are absorbent articles comprising a top layer, a middle absorbent layer, and a bottom layer, wherein the middle absorbent layer comprises a fluid drawing material and a fluid storage material, wherein the fluid drawing material comprises electrospun nanofibers. In some embodiments, disclosed herein are absorbent articles comprising a top layer, a middle absorbent layer, and a bottom layer, wherein the top layer comprises one or more channels anchored from the top layer through the middle absorbent layer and into the bottom layer, wherein the middle absorbent layer comprises a fluid drawing material and a fluid storage material, and wherein the fluid storage material comprises superabsorbent polymer.

In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the one or more channels are arranged in a parallel orientation to a longitudinal axis of the absorbent article. In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the one or more channels are arranged such that a distance from a midline of the absorbent article to the one or more channels varies along a length of the one or more channels. In some embodiments, disclosed herein are absorbent articles comprising a top layer, a middle absorbent layer, and a bottom layer, wherein the top layer comprises one or more channels anchored from the top layer through the middle absorbent layer and into the bottom layer, wherein the one or more channels extend over no more than 66% of a length of the absorbent article. In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the one or more channels extend over no more than 75% of a length of the absorbent article. In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the one or more channels penetrate to a depth of no more than 50% of a thickness of the absorbent article. In some embodiments, disclosed herein are absorbent articles having a thickness of no more than one millimeter. In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the bottom layer comprises an adhesive region on a side opposite to a side in contact with the middle absorbent layer. In some embodiments, the adhesive region on a side opposite to a side in contact with the middle absorbent layer is in contact with a protection paper. In some embodiments, the protection paper is attached to a wrapper element. In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the absorbent article is folded such that the folded absorbent article is completely enclosed by a wrapper element.

In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the absorbent article is a menstrual pad about 155 millimeters long and about 60 millimeters wide. In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the absorbent article is a menstrual pad about 225 millimeters long and about 80 millimeters wide. In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the absorbent article is a menstrual pad about 305 millimeters long and about 85 millimeters wide. In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the absorbent article is a bladder liner about 200 millimeters long and about 90 millimeters wide at one end and 65 millimeters wide at an opposite end. In some embodiments, disclosed herein are absorbent articles comprising a top layer, a middle absorbent layer, and a bottom layer, wherein the top layer comprises one or more channels anchored from the top layer through the middle absorbent layer and into the bottom layer, and wherein the absorbent article is for use by a wearer to absorb bodily fluid. In some embodiments, the wearer is female.

In some embodiments, disclosed herein are methods of making absorbent articles, the methods comprising forming an absorbent article comprising a top layer, a middle absorbent layer, and a bottom layer, and anchoring one or more channels in the top layer anchored through the middle absorbent layer and into the bottom layer. In some embodiments, the anchoring one or more channels in the top layer through the middle absorbent layer and into the bottom layer comprises ultrasonic welding.

BRIEF DESCRIPTION OF THE DRAWINGS

FIG. 6A depicts application of fluid to an exemplary ultrathin absorbent hygienic pad; FIG. 6B is an image 7 seconds after application of fluid; FIG. 6C is an image 14 seconds after application of fluid; and FIG. 6D is an image 22 seconds after application of fluid.

FIG. 7A depicts initial application of fluid to an exemplary ultrathin absorbent hygienic pad; FIG. 7B is an image 60 seconds after initial application of fluid; FIG. 7C is an image 90 seconds after initial application of fluid; and FIG. 7D is an image 170 seconds after initial application of fluid. Additional fluid was added during the course of the experiment.

DETAILED DESCRIPTION

Figure 1:
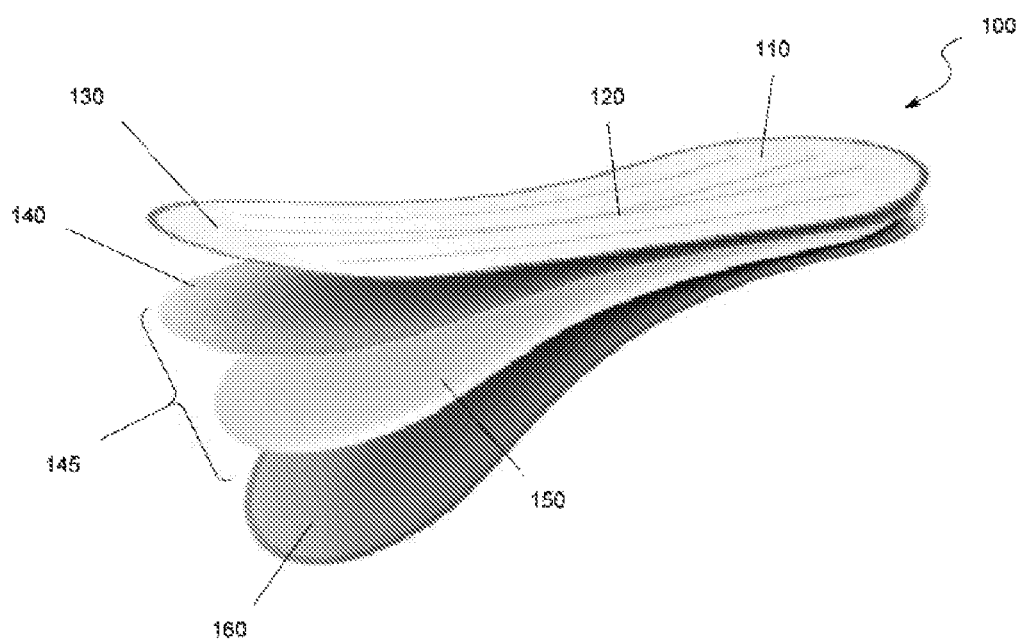
FIG. 1 shows an embodiment of the ultrathin absorbent hygienic pads disclosed herein, depicting a perspective view of an ultrathin absorbent hygienic pad having a top layer, a middle absorbent layer, and a bottom layer, with channels anchored from the top layer through the middle absorbent layer and into the bottom layer.

Absorbent articles serve hygienic purposes, including the absorption of urine and menstrual discharge as well as protecting the body of the wearer from irritation due to prolonged contact with fluid. Absorbent articles include, among others, adult incontinence pads/briefs, panty liners, sanitary napkins, menstrual pads, catamenial products, feminine hygiene products, and diapers. Such absorbent articles may be intended to be discarded after a single use ("disposable" absorbent articles) or may be intended for multiple uses.

The structure and particular absorbent core composition of ultrathin highly absorbent articles can vary. Ultrathin absorbent articles generally have a thickness that is less than 5 millimeters and utilize wicking material that draws fluid away from the skin of the wearer and directs the fluid to an absorbent layer where the fluid is absorbed and stored. Absorbent articles may utilize superabsorbent polymer (SAP) material that operates to absorb and store the fluid. Unfortunately, such absorbent articles often do not operate with a desired efficiency and effectiveness because absorbing material present in the absorbent article can reach a maximum absorption and storage capacity and fail to absorb additional fluid. While absorbing material, such as SAP material, can be added, such additional material is undesirable as it significantly increases the cost of the absorbent article as well the thickness of the absorbent article. In addition, while additional absorbing material operates to increase the amount of fluid that can be absorbed and stored, unless the absorbing material, such as SAP material, is in direct contact with the fluid to be absorbed, the rate of absorption is not maximized.

Furthermore, absorbent articles such as hygienic pads using SAP material have decreased fluid absorption rates when the SAP material becomes fully saturated at or near the point where fluid is introduced to the absorbent article. This may cause the SAP material to form "gel blocks" or "speed bumps" that operate to reduce or prevent fluid absorption. In order to improve the flow of fluids in saturated SAP material, surface cross-linkers can be added to the SAP material to improve the absorbency of the SAP material. Unfortunately, in many applications the use of such cross-linkers still does not provide sufficient or desired absorbency of the SAP material. Further, fluid to be absorbed often does not reach the location necessary for making contact with unsaturated portions of the SAP material, thereby not fully utilizing the SAP material within the absorbent pad and reducing the absorbent article's efficiency and effectiveness. As such, dispersing fluid across the entire area of an absorbent article allows maximum utilization of the absorbing material present in the absorbent article. However, dispersion of fluid across the entire area of an absorbent article should not come at the cost of fluid leaking at the periphery of the absorbent article.

Provided herein are absorbent articles, including ultrathin absorbent hygienic pads. As disclosed herein, "absorbent articles," ultrathin absorbent hygienic pads, "ultrathin pads," and "absorbent pads," refer to articles that are effective for absorbing and containing bodily fluids, including fluids emitted from the body of a user. The absorbent articles disclosed herein may be placed against or in proximity to the body of a user and operate to absorb and contain bodily fluids emitted from the user, including bodily fluids such as urine and menstrual fluid. The absorbent articles disclosed herein may comprise a top layer, a middle absorbent layer, and a bottom layer, and the top layer may comprise one or more channels anchored from the top layer through the middle absorbent layer and into the bottom layer. In some embodiments, the absorbent articles described herein are worn by a user and used to absorb bodily fluids, including absorbent articles worn by a human and used to absorb bodily fluids including urine and menstrual fluid. Also disclosed herein are methods of making an absorbent article comprising forming an absorbent article comprising a top layer, a middle absorbent layer, and a bottom layer, and then anchoring one or more channels from the top layer through the middle absorbent layer and into the bottom layer. In some embodiments, ultrasonic welding is used to anchor the one or more channels from the top layer through the middle absorbent layer and into the bottom layer.

Absorbent Articles

Disclosed herein, in certain embodiments, are absorbent articles comprising a top layer, a middle absorbent layer, and a bottom layer, wherein the top layer comprises one or more channels anchored from the top layer through the middle absorbent layer and into the bottom layer. The channels of the absorbent articles disclosed herein are anchored such that the channel remains functionally intact even as fluid is added to the absorbent article, in contrast to non-anchored channels (such as embossed channels) which lose their structure as they swell with fluid. As fluid is added to the absorbent articles disclosed herein, the channels provide a higher contrast in depth and density to that of the material surrounding the channels. As the material surrounding the channels begins to absorb and swell with fluid, the channels provide a travel path for the fluid that is lower friction and improves the distribution of fluid. In some embodiments, the absorbent articles disclosed herein are configured to absorb menstrual fluid. In some embodiments, the absorbent articles disclosed herein are configured to absorb urine. Due to differences in variables including composition, volume, speed of dispersion, and viscosity, absorbent articles disclosed herein configured to absorb menstrual fluid may differ in their structural components from absorbent articles disclosed herein configured to absorb urine. Menstrual fluid often comprises blood, cervical mucus, vaginal secretions, and endometrial tissue, and is thus more viscous than urine. Additionally, urine is emitted at a much higher speed and greater volume than menstrual fluid. The speed and volume of menstrual fluid can range from a small amount (such as 0.1 to 2 ml per hour) to a few milliliters emitted in a few seconds. The speed and volume of menstrual fluid emitted can thus range from a trickle to a gush. Higher amounts of menstrual fluid emission can occur following accumulation of menses in the vagina which can exit the body upon a change in position, such as a transition from standing to sitting. Regardless, the total amount of menstrual fluid to be absorbed by absorbent articles configured to acquire menstrual fluid is still less than the total amount of urine to be absorbed by absorbent articles configured to acquire urine. Further, the absorbent articles disclosed herein configured to acquire menstrual fluid may differ in their structural components from the absorbent articles disclosed herein configured to acquire urine due to the differences between the skin of the vulvar area of a female and the skin of the genitals of a male.

In some embodiments, absorbent articles disclosed herein configured to acquire urine may comprise components which neutralize the pH of acidic urine and may be configured to acquire a higher volume of urine than the absorbent articles disclosed herein configured to acquire menstrual fluid. In some embodiments, absorbent articles disclosed herein configured to acquire urine may comprise absorbent material situated to absorb fluid emitted from the front of a wearer's body. In some embodiments, absorbent articles disclosed herein configured to acquire menstrual fluid may comprise absorbent material situated to absorb fluid emitted from the center of a wearer's body.

Further disclosed herein are absorbent articles comprising a top layer, a middle absorbent layer, and a bottom layer, wherein the top layer comprises one or more channels anchored from the top layer through the middle absorbent layer and into the bottom layer, and wherein the absorbent article further comprises "wings" or "flaps" disposed perpendicular to a longitudinal axis of the absorbent article. In some embodiments, the absorbent articles disclosed herein comprise a body-facing surface intended to be worn or positioned toward or adjacent the body of a user, and a garment-facing surface intended to be worn or positioned adjacent toward or adjacent the undergarments of a user or to come into contact with the hand of a user when placing the absorbent article into position for use.

In some embodiments, the absorbent articles disclosed herein comprise materials suitable for use hygienic pads and bladder liners. Suitable materials for hygienic pads and bladder liners are non-irritating, durable, and flexible and include, by way of non-limiting examples, textiles of natural fiber (e.g., cotton, linen, and hemp), textiles of synthetic fiber (e.g., nylon, polyester, aramid, olefin, and acrylic), and plastic (e.g., polyvinyl chloride, low-density polyethylene, and polypropylene). In some embodiments, the absorbent articles disclosed herein comprise one or more of a skin treatment agent, a skin protective agent, or an odor-absorbing agent. In some embodiments, the absorbent articles disclosed herein comprise absorbent article packaging and release liner systems. Suitable materials for absorbent article packaging and release liner systems are easily torn and include, by way of non-limiting examples, cloth, paper, and waxed paper. In some embodiments, the absorbent articles disclosed herein comprise an adhesive that bonds the absorbent article to the inside of a wrapper. In some embodiments, the absorbent articles disclosed herein comprise an adhesive that bonds a release liner adhered to a bottom layer of the absorbent article to the inside of a wrapper. In some embodiments, the absorbent articles disclosed herein comprise an adhesive that bonds a release liner adhered to a bottom layer of the absorbent article to the inside of a wrapper and the absorbent article is folded such that the wrapper completely envelopes the absorbent article.

In some embodiments, the absorbent articles disclosed herein are dimensioned to fit different parts of the body, such as absorbent articles dimensioned to cover human genitals. In some embodiments, the absorbent articles disclosed herein are dimensioned in standard sizes, including for example, 150 mm long×50 mm wide, 150 mm long×55 mm wide, 150 mm long×60 mm wide, 150 mm long×65 mm wide, 150 mm long×70 mm wide, 150 mm long×80 mm wide, 150 mm long×85 mm wide, 150 mm long×90 mm wide, 160 mm long×55 mm wide, 225 mm long×80 mm wide, 305 mm long×85 mm wide, 200 mm long×90 mm wide, or sizes in-between any of these exemplary sizes. In some embodiments, the absorbent articles disclosed herein are 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 250, or more millimeters long or wide, including increments therein. In some embodiments, the absorbent articles disclosed herein are less than 2000, 1900, 1800, 1700, 1600, 1500, 1400, 1300, 1200, 1100, 1000, 975, 950, 925, 900, 875, 850, 825, 800, 775, 750, 725, 700, 675, 650, 625, 600, 575, 550, 525, 500, or less micrometers thick, including increments therein. In some embodiments, suitable shapes for the absorbent articles disclosed herein include hourglass, teardrop, square, rectangular, oval, round, triangle, and butterfly-shaped. The size and shape of the absorbent articles disclosed herein can be altered to meet absorbent capacity requirements and to provide comfort to the user or wearer.

Bottom Layers

In some embodiments, the absorbent articles described herein comprise a bottom layer. The bottom layer may comprise any suitable and effective material, provided that the bottom layer prevents external leakage of fluid absorbed and contained in the absorbent article. Suitable bottom layer material may include, but are not limited to, woven and nonwoven materials, laminated tissue, polymeric films such as thermoplastic films of polyethylene and/or polypropylene, composite materials such as film-coated nonwoven material, and combinations thereof. In some embodiments, the bottom layer is made from polyurethane (PU). In some embodiments, the bottom layer is made from film. In some embodiments, the bottom layer is transparent. In some embodiments, the bottom layer is made from backing film or a strikethrough film. In some embodiments, the bottom layer is printed. In some embodiments, the bottom layer comprises an adhesive on its garment-facing surface. In some embodiments, the absorbent articles disclosed herein comprise a bottom layer with an adhesive on the garment-facing side protected by a release liner. Upon removal of the release liner, a user may adhere the absorbent article to the user's undergarments to avoid shifting of the absorbent article during movement.

In some embodiments, the bottom layer is made from a suitable pliable liquid-impervious material. Suitable material for the bottom layer of the absorbent articles disclosed herein includes films of polyethylene, polypropylene, polyester, nylon, polyvinyl chloride, polyethylene polypropylene, and blends of these materials, polymeric films, thermoplastic film and film-coated nonwoven materials. For example, the bottom layer can be made of a polyethylene film having a thickness in the range of 0.02-0.04 mm. The bottom layer may be pigmented with, for example, titanium dioxide, to provide a pleasing color or to render the bottom layer opaque enough that bodily fluids being contained by the absorbent article are not visible. In addition, the bottom layer may be formed in such a manner that it is opaque, for example, by using various inert components in the polymeric film and then biaxially stretching the film. The bottom layer preferably has sufficient liquid imperviousness to prevent any leakage of fluids and should also have sufficient flexibility such that it will easily conform to the shape of the wearer's body and be sufficiently sized to prevent leakage of fluid.

Top Layers

In some embodiments, the absorbent articles described herein comprise a top layer, a middle absorbent layer, and a bottom layer, wherein the top layer comprises one or more channels anchored from the top layer through the middle absorbent layer and into the bottom layer. The top layer may comprise any suitable and effective material, provided that the top layer provides a soft, compliant, and non-irritating sensation to the wearer's skin. Suitable top layer materials include liquid pervious materials oriented towards and in contact with the body of the wearer which permit bodily discharges to rapidly penetrate through the top layer without allowing fluid to flow back through the top layer to contact the skin of the wearer. Suitable top layer material can include, without limitation, woven and nonwoven materials, apertured film materials including apertured formed thermoplastic films, apertured plastic films, and fiber-entangled apertured films, hydro-formed thermoplastic films, porous foams, reticulated foams, reticulated thermoplastic films, thermoplastic scrims, and combinations thereof.

In some embodiments, the top layer comprises a nonwoven spun sheet bound to an aperture layer. In some embodiments, the top layer comprises silicone adhesive, hydrocolloid adhesive, polyurethane adhesive, rubber-based adhesive, acrylic adhesive, coated woven material, hydrogel adhesive, and combinations thereof. In some embodiments, the aperture layer comprises a plurality of holes, cuts, slits, apertures, perforations, discontinuities, and/or bevels. In some embodiments, the distribution and spacing of the holes, cuts, slits, apertures, perforations, discontinuities, and/or bevels are regularly arranged with a separation substantially greater than their area. In some embodiments, the holes, cuts, slits, apertures, perforations, discontinuities, and/or bevels are in a shape selected from a circle, a square, a rectangle, a triangle, an oval, a pentagon, a hexagon, and a rounded rectangle. In some embodiments, the holes, cuts, slits, apertures, perforations, discontinuities, and/or bevels are circular and between 0.1 mm and 5 mm, or between 0.5 mm and 2 mm. In some embodiments, the spacing between the holes, cuts, slits, apertures, perforations, discontinuities, and/or bevels is between 0.2 and 10 mm. In some embodiments, the number of holes, cuts, slits, apertures, perforations, discontinuities, and/or bevels per unit area is between 1 and 100, or between 1 and 50, or between 1 and 20 per square centimeter.

In some embodiments, the absorbent articles disclosed herein comprise a top layer, a middle absorbent layer, and a bottom layer, wherein the top layer comprises one or more channels anchored from the top layer through the middle absorbent layer and into the bottom layer and the top layer comprises an apertured plastic film that is non-absorbent and pervious to bodily fluids and provides for minimal or no flow of bodily fluid back through the top layer. The top layer may comprise woven and nonwoven materials, of which non-limiting examples include fibrous materials made from natural fibers, modified natural fibers, synthetic fibers, or combinations thereof. Fibrous materials include hydrophilic fibrous materials and hydrophobic fibrous materials. In some embodiments, the top layer comprises a hydrophobic material, or a material that has been rendered hydrophobic. In some embodiments, portions of the top layer can be rendered hydrophilic. The top layer can comprise hydrophilic fibers, hydrophobic fibers, or combinations thereof. In some embodiments, the top layer comprises a nonwoven fibrous material in the form of a nonwoven web, such as a nonwoven web producing by methods including spinbonding, carding, wat-laying, air-laying, meltblowing, needle-punching, mechanical entangling, thermo-mechanical entangling, and hydroentangling. In some embodiments, the top layer may comprise a low basis weight nonwoven materials, such as a nonwoven material having a basis weight of from about 18 $g/m^2$ to about 25 $g/m^2$. In some embodiments, the top layer further comprises a skin treatment agent or skin protective agent, such as a lotion or a moisturizer.

In some embodiments, the top layer comprises a non-woven liner sheet material which readily allows the passage of liquids to the underlying middle absorbent layer. Examples of suitable liner sheet materials include nonwoven spun-bond or carded webs of polypropylene, polyethylene, nylon, polyester and blends of these materials. In some embodiments, the top layer comprises a top sheet formed from an air laid material. The top sheet, top layer, middle absorbent layer, and bottom layer can be attached together by means of lamination using an adhesive. The lamination can be throughout the entire pad or at one or more locations, such as along or close to the peripheral edges of the components. The top sheet operates to fit against the wearer's body to provide a compliant, soft feeling and non-irritating surface against the skin of a wearer and is pervious to fluids to allow fluid to penetrate the top sheet. In some embodiments, the top layer comprises a plurality of embedded holes that operate as micro-funnels to capture and help channel bodily fluid from an upper top surface of the top layer to the middle absorbent core thereby increasing the rate of fluid being directed to the middle absorbent layer. In some embodiments, the top layer comprises an air laid material, a cold-strued non-woven material, a non-woven spun-bond or carded web of polyester (including, but not limited to Rayon, polypropylene, and polyethylene terephthalate (PET)), or a combination thereof. In some embodiments, the top layer comprises woven and nonwoven materials comprising natural fibers, synthetic fibers or a combination thereof, porous thermoplastic and plastic films, hydroformed or reticulated thermoplastic films or other conventional materials.

Absorbent Layers

In some embodiments, the absorbent articles described herein comprise a top layer, a middle absorbent layer, and a bottom layer, wherein the top layer comprises one or more channels anchored from the top layer through the middle absorbent layer and into the bottom layer. In some embodiments, the middle absorbent layer is positioned between the top layer and the bottom layer. In some embodiments, the top layer and the middle absorbent layer are bonded together with an adhesive. The middle absorbent layer may comprise any material or combination of materials suitable for absorbing, distributing, and storing aqueous fluids such as urine, blood, menses, and water found in body exudates. In some embodiments, the middle absorbent layer comprises a fluid drawing material and a fluid storage material. The fluid storage material may be configured or constructed to meet absorbent capacity requirements. Non-limiting examples of fluid storage materials suitable for use in the absorbent articles disclosed herein include comminuted wood pulp (also known as "fluff pulp"), creped cellulose wadding, absorbent gelling materials including superabsorbent polymers such as hydrogel-forming polymeric gelling agents, chemically stiffened, modified, or cross-linked cellulose fibers, meltblown polymers including coform, synthetic fibers including crimped polyester fibers, tissue including tissue wraps and tissue laminates, capillary channel fibers, absorbent foams, absorbent sponges, synthetic staple fibers, alginate fibers, chitosan or chitosan derivative fibers, acrylic fibers, non-gelling fibers, superabsorbent fibers, sphagnum moss, equivalent materials, or combinations thereof. In some embodiments, the middle absorbent layer comprises an antimicrobial fiber, such as an antimicrobial fiber comprising silver ions or metal ions.

In some embodiments, the middle absorbent layer comprises superabsorbent polymer. In some embodiments, the superabsorbent polymer is carboxymethylcellulose fiber with a degree of substitution between 0.1 and 0.5 carboxymethyl groups per cellulose unit. In some embodiments, the superabsorbent polymer is an acrylic fiber which incorporates a co-monomer and provides dye-sites in the fiber. In some embodiments, the co-monomer is selected from the group consisting of itaconic acid and 2-acrylamido methyl propane sulphonic acid. Where the fiber is an alginate fiber, it may be a calcium alginate fiber or a mixed metal alginate fiber such as a calcium/sodium alginate fiber. The alginate polymer may be one with a high mannuoronate or a high guluronate. In some embodiments, the absorbent articles disclosed herein comprise a middle absorbent layer comprising chemically modified cellulose. In some embodiments, the absorbent articles disclosed herein comprise a middle absorbent layer comprising, for example, carboxymethylcellulose, carboxyethylcellulose, or other chemically modified cellulose.

In some embodiments, the absorbent articles described herein absorb fluid from a body. In some embodiments, the absorbent articles described herein comprise a middle absorbent layer with a minimum level of absorbency. In some embodiments, the absorbency of the absorbent articles described herein may be measured by the free swell absorbency method. In some embodiments, the absorbency of the absorbent articles described herein is at least 0.30 $g/cm^2$, or at least 0.40 $g/cm^2$, or at least 0.50 $g/cm^2$, or at least 0.60 $g/cm^2$, or at least 0.70 $g/cm^2$, or at least 0.80 $g/cm^2$, or at least 0.90 $g/cm^2$, or at least 1.0 $g/cm^2$, or at least 1.1 $g/cm^2$, or at least 1.2 $g/cm^2$, or at least 1.3 $g/cm^2$, or at least 1.5 $g/cm^2$, or at least 2.0 $g/cm^2$, or at least 2.5 $g/cm^2$. In some embodiments, the absorbent articles described herein comprise a gelling fiber, an absorbent fiber, or a hydrophilic foam. In some embodiments, the absorbent articles disclosed herein comprise a middle absorbent layer comprising a material selected from the group consisting of foam, polyurethane foam, absorbent textiles, hydrogels, superabsorbent fibers, superabsorbent polymers, superabsorbent powder-fiber blends, and mixtures thereof. In some embodiments, the middle absorbent layer comprises a gelling blend of a material selected from the group consisting of foam, polyurethane foam, absorbent textiles, hydrogels, superabsorbent fibers, superabsorbent polymers, superabsorbent powder-fiber blends, and mixtures thereof. In some embodiments, the middle absorbent layer comprises a non-gelling blend of a material selected from the group consisting of foam, polyurethane foam, absorbent textiles, hydrogels, superabsorbent fibers, superabsorbent polymers, superabsorbent powder-fiber blends, and mixtures thereof. In some embodiments, the middle absorbent layer comprises low density cross-linked superabsorbent polymer. Low density cross-linked superabsorbent polymers generally have a high absorbent capacity and swell to a larger degree with a softer and stickier gel formation. In some embodiments, the middle absorbent layer comprises high density cross-linked superabsorbent polymer. High density cross-linked superabsorbent polymers exhibit lower absorbent capacity and swell, but their gel strength is firmer and can maintain particle shape even under modest pressure.

In some embodiments, the absorbent articles described herein comprise a top layer, a middle absorbent layer, and a bottom layer, wherein the top layer comprises one or more channels anchored from the top layer through the middle absorbent layer and into the bottom layer, and wherein non-SAP-containing roll good materials such as latex or thermally bonded air laid fluff pulp, or synthetic spun-bonded, carded, or hydro-entangled non-woven material may be positioned above or below the middle absorbent layer. In some embodiments, the middle absorbent layer comprises a central fibrous layer containing 50-95% by weight particulate or fibrous superabsorbent polymer (SAP) and at least one other fibrous or particulate material that is capable of maintaining high SAP efficiency. High SAP concentrations can also provide thinner absorbent cores that can provide new options for product design. The middle absorbent layer can be made using either a wet or a dry process.

In some embodiments, the middle absorbent layer comprises a fluid drawing material conjoined with a fluid storage material. In some embodiments, the fluid storage material is in the form of a fluid storage material layer. In some embodiments, the fluid storage material is laminated together with the fluid drawing material along their periphery edges. It should be understood that other means such as adhesives can be used to conjoin the fluid drawing material with the fluid storage material layer. In some embodiments, the fluid drawing material operates to draw the bodily fluid penetrating a top layer comprising a top sheet to the fluid storage material layer, such as by wicking or capillary action which them spreads the fluid across the fluid storage material layer, such as by wicking or capillary action. In some embodiments, the fluid drawing material and the fluid storage material are the same material that operates to spread fluid across and into the material by wicking or capillary action. In another embodiment, the fluid storage material is a superabsorbent polymer (SAP) material which when the fluid contacts the SAP material it is converted into gel thereby locking the bodily fluid away from the top layer and reducing the likelihood of fluid buildup along the surface of the wearer's body or leakage of fluid out of the absorbent pad.

In some embodiments, the middle absorbent core comprises a fluid drawing material and a fluid storage material in the form of superabsorbent polymer (SAP) packets (clumps or particles) creating a plurality of fluid reservoirs that are incorporated into and throughout the fluid drawing material. In some embodiments, the fluid drawing material is formed from a material having hydrophobic properties that operates to guide fluid, such as by wicking or capillary action, for contacting the fluid reservoirs such that the super absorbent material converts the fluid into a gel. It should be understood that the geometry and the number of SAP packets forming fluid reservoirs are such to maximize the absorbing surface (surface that fluid cones into contact with) thereby increasing the rate that fluid is turned into a gel while reducing the likelihood of creating "gel blocks" reducing fluid absorption. In some embodiments, the fluid storage material layer or the fluid reservoirs are formed from a super absorbent polymer (SAP) material or slush powders, hydrogels, or other super-absorbent material(s). In some embodiments, the fluid drawing material is formed from a material(s) having hydrophobic properties positioned that operates to guide fluid, such as by wicking or capillary action, for absorption into the fluid storage material layer or fluid reservoirs. Such materials include, but are not limited to, spun-laced fabric made from a combination of cellulosic fibers, such as but not limited to Viscose or wet-laid cellulose pulp material preferably comprising soft wood pulp (having fibers of sufficient length to provide the necessary wicking of the fluid to be absorbed by the fluid storage material layer) or rayon or lyocell, synthetic fibers, such as but not limited to polyester fibers. In some embodiments, the fluid drawing layer contains about 50-95% by weight particulate or fibrous superabsorbent polymer (SAP) and at least one other fibrous or particulate material that is capable of maintaining high SAP efficiency.

In some embodiments, the absorbent articles disclosed herein comprise a middle absorbent layer comprising a fluid drawing material and a fluid storage material, wherein the fluid drawing material is electro-spun nanofibers, such as natural polymers or polymer blends creating a high porous media. In some embodiments, the nanofibers include superabsorbent material packets deposited throughout and held in place by the fibers that operate as fluid reservoirs and operate to convert bodily fluid into a gel.

Channels

In some embodiments, the absorbent articles described herein comprise a top layer, a middle absorbent layer, and a bottom layer, wherein the top layer comprises one or more channels anchored from the top layer into the middle absorbent layer. In some embodiments, the channels are anchored via ultrasonic welding, pressure, heat, a combination of heat and pressure, heat-pressing, embossing, stapling, sewing, melting, or a combination of any of these techniques. In some embodiments, the channels are anchored via ultrasonic welding. In some embodiments, the channels are anchored via heat. In some embodiments, the channels are anchored via pressure. In some embodiments the channels are anchored via a combination of heat and pressure. The channels of the absorbent articles disclosed herein are anchored such that the channel remains functionally intact even as fluid is added to the absorbent article. As fluid is added, the channels provide a higher contrast in depth and density to that of the material surrounding the channels. As the material surrounding the channels begins to absorb and swell with fluid, the channels provide a travel path for the fluid that is lower friction and improves the distribution of fluid. In some embodiments, the absorbent articles disclosed herein comprise a top layer, a middle absorbent layer comprising fluid drawing material and fluid absorbing material, and a bottom layer, wherein the top layer comprises one or more channels anchored from the top layer into and through the fluid drawing material and fluid absorbing material, and into the top of the bottom layer. Thus, in some embodiments, the absorbent articles disclosed herein comprise channels bonded through all layers of the absorbent article which allows the channel to distribute fluid more effectively into areas lacking channels. The absorbent articles comprising anchored channels disclosed herein provide superior fluid distribution than absorbent articles with non-anchored channels, such as absorbent articles with embossed lines or patterns. This is because as soon as a non-anchored channel begins to absorb fluid, it swells concurrently with the rest of the absorbent article and provides no differentiation for directional dispersion of fluid. The anchored channels of the absorbent articles disclosed herein provide a contrast of both density and space from the areas of the absorbent article lacking anchored channels which allows fluid to be directed along the length of the channel, leading to an increase in distribution and absorption of the fluid. This contrast is maintained even as the areas of the absorbent article lacking anchored channels begin to swell from the absorption of fluid.

In some embodiments, the absorbent articles disclosed herein comprise a top layer, a middle absorbent layer, and a bottom layer, wherein the top layer comprises one or more channels anchored from the top layer through the middle absorbent layer and into the bottom layer, wherein the one or more channels are anchored via ultrasonic welding from the top layer through the middle absorbent layer and into the bottom layer, and wherein the one or more channels are arranged in a parallel orientation to a longitudinal axis of the absorbent article. In some embodiments, the one or more channels are arranged such that a distance from a midline of the absorbent article to the one or more channels varies along a length of the one or more channels, such as an embodiment where the one or more channels converge toward the midline at one end of the absorbent article and diverge from the midline at the opposite end of the absorbent article. In some embodiments, the one or more channels are arranged such that the channel orientation mimics the shape of the absorbent article. In some embodiments, the one or more channels are arranged such that the channels are perpendicular to a longitudinal axis of the absorbent article. In some embodiments, the one or more channels extend over almost the entire length of the absorbent article. In some embodiments, the one or more channels extend over 99%, 98%, 97%, 96%, 95%, 90%, 85%, 80%, 75%, 70%, 69%, 68%, 67%, 66%, 65%, 64%, 63%, 62%, 61%, 60%, 55%, 50%, 45%, 40%, 35%, 30%, 25%, 20%, 15%, or 10% of a longitudinal length of the absorbent article. In some embodiments, the absorbent articles disclosed herein comprise a top layer, a middle absorbent layer, and a bottom layer, wherein the top layer comprises one or more channels anchored from the top layer through the middle absorbent layer and into the bottom layer, and wherein the channels penetrate to a depth of no more than 10%, 15%, 20%, 25%, 30%, 35%, 40%, 45%, 50%, 55%, 60%, 65%, 70%, 75%, 80%, 85%, or 90% of a thickness of the absorbent article. In some embodiments, the channels of the absorbent articles disclosed herein penetrate to a depth of no more than 500 micrometers into an absorbent article that is 1000 micrometers thick. In some embodiments, the absorbent articles disclosed herein comprise one or more channels. In some embodiments, the absorbent articles disclosed herein comprise two or more channels. In some embodiments, the absorbent articles disclosed herein comprise three or more channels. In some embodiments, the absorbent articles disclosed herein comprise four or more channels. In some embodiments, the absorbent articles disclosed herein comprise 5, 6, 7, 8, 9, 10, 11, 12, 13, 14, 15, 16, 17, 18, 19, 20, or more channels.

In some embodiments, the absorbent articles described herein comprise channels formed by ultrasonic welding. Ultrasonic welding allows melting of materials by means of ultrasonic vibrations so that a cohesive or form-fit joint is produced. Ultrasonic welding comprises the use of an anvil and an ultrasonic horn. Two materials are placed between the anvil and the ultrasonic horn and ultrasonic vibration is applied to the ultrasonic horn to weld the materials together.

Adhesives

In some embodiments, the absorbent articles described herein comprise an adhesive. In some embodiments, the adhesive serves to hold the absorbent article to the clothing of a user. In some embodiments, the adhesive is protected by a release liner which is removed in order to expose the adhesive. In some embodiments, the adhesive serves to bind two or more of a top layer, a middle absorbent layer, and a bottom layer of the absorbent article together. In some embodiments, the adhesive comprises a silicone adhesive. The adhesive may also be a hydrocolloid, polyurethane, rubber based adhesive or acrylic adhesive. In some embodiments, the top layer, middle absorbent layer, and bottom layer are thermally, ultrasonically, or chemically bonded to one another. In some embodiments, the top layer, middle absorbent layer, and bottom layer are joined using lines of hot melt adhesive or mechanical fasteners such as thread, clips, or staples. In some embodiments, a hydrophilic adhesive is used to join the top layer, the middle absorbent layer, and the bottom layer.

In some embodiments, the absorbent articles disclosed herein comprise a top layer, a middle absorbent layer, and a bottom layer, wherein the top layer comprises one or more channels anchored from the top layer through the middle absorbent layer and into the bottom layer, and wherein the top layer, the middle absorbent layer, and the bottom layer are integrally bonded together by a lamination or by a bonding material applied as a hot melt glue (such as a synthetic rubber based pressure sensitive hot melt adhesive), or a cold glue, or as a mixture of polyvinyl alcohol (PVOH) mixed with Kymene or a Kymene equivalent that integrally secures the top layer, middle absorbent layer, and the bottom layer together or such that they are bonded together along their peripheral edges. The layers may be joined using hot melt extrusion, lamination, and other processes and systems suitable for integrally securing the layers together. In some embodiments, a hydrophilic adhesive is used to join the top layer to the bottom layer. The particular joining method may be dictated by the types of materials selected for attaching the top layer, middle absorbent core and the bottom layer together Ultrathin Absorbent Hygienic Pads In some embodiments, provided herein are absorbent articles comprising ultrathin absorbent hygienic pads. Such an ultrathin absorbent hygienic pad is depicted in FIG. 1, where an exemplary ultrathin absorbent hygienic pad 100 is shown as including a top layer 110 and a bottom layer 160, which may be substantially coterminous with the top layer 110. When the ultrathin absorbent hygienic pad is being worn, the top layer 110 faces the wearer's body and the bottom layer 160 faces away from the wearer. A middle absorbent layer 145 is placed coterminously between the top layer 110 and the bottom layer 160.

As shown in FIG. 1, the top layer 110 can includes a non-woven spun sheet attached to an aperture layer 130 providing a soft feeling against the skin of a wearer. The aperture layer 130 may include embedded micro-funnels forming channels 120, which help in capturing bodily fluids. The bottom layer 160 can include a polymer sheet, which prevents any leakage of fluids from the bottom layer. The middle absorbent layer 145 can include an air laid layer 140 conjoined with a laminate superabsorbent polymer layer 150. The air laid layer 140 may help in channeling the fluid from the top layer to the laminate super absorbent polymer layer 150, which converts fluid into gel to lock it away from the top layer 110.

Figure 2:
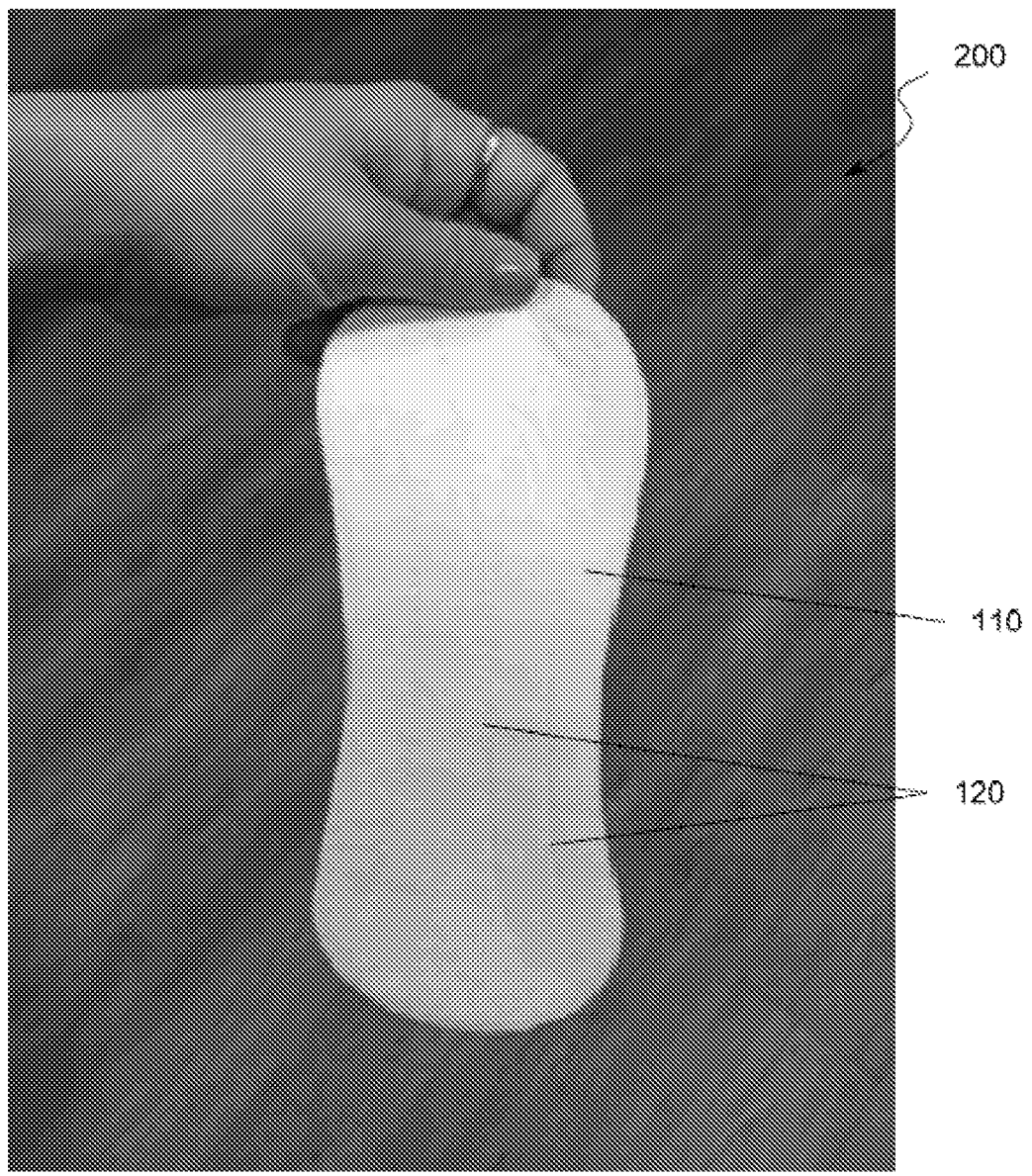
FIG. 2 shows a planar view of an exemplary ultrathin absorbent hygienic pad as disclosed herein, showing the channels anchored from the top layer through the middle absorbent layer and into the bottom layer.
Figure 3:
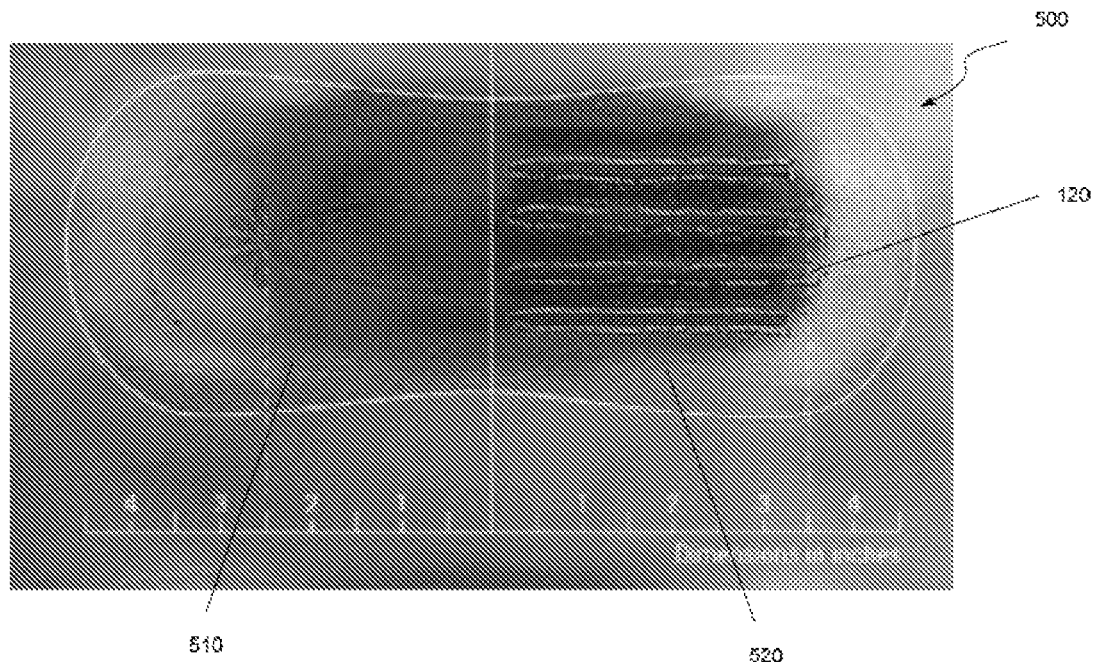
FIG. 3 shows a forward-looking infrared (FLIR) image of an ultrathin absorbent hygienic pad as disclosed herein with channels present in the right-hand section of the pad and no channels present in the left-hand section of the pad.
Figure 4:
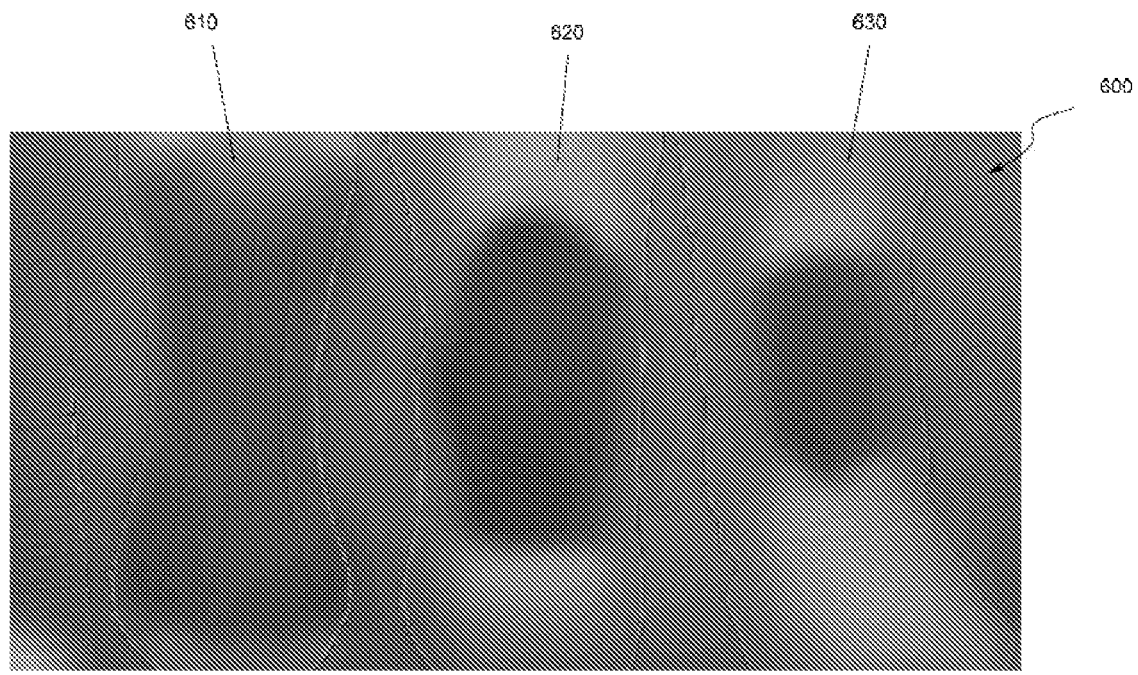
FIG. 4 shows a forward-looking infrared (FUR) image of three absorbent pads, the left-hand pad is an embodiment of the ultrathin absorbent hygienic pads disclosed herein, and the middle and right-hand pads are not embodiments of the ultrathin absorbent hygienic pads disclosed herein.

FIG. 2 illustrates a front side view 200 of an exemplary ultrathin absorbent hygienic pad 100. The top layer 110 with channels 120 can be visualized. FIG. 3 illustrates a forward looking infrared (FLIR) image of an absorbent pad with extensive absorption seen in the embodiment of the ultrathin absorbent hygienic pad comprising channels disclosed herein (right-hand side of FIG. 3). The extent of absorption on a prior art absorbent pad 510 (left-hand side of FIG. 3) in significantly less than the extent of absorption on absorbent pad 520 in accordance with the disclosure herein. The channels in absorbent pad 520 result in higher absorption in the longitudinal direction of the absorbent pad. FIG. 4 illustrates an FLIR image of an absorbent pad 610 in accordance with the disclosure herein showing extensive absorption in comparison to prior art absorbent pad 620 and prior art absorbent pad 630 without a channeled structure formed by anchored grooves. Each pad in FIG. 4 received the same amount of fluid (approximately 45 milliliters) applied at the center of the pad, and the image was taken after a short period of time had elapsed (approximately 2 minutes). The anchored channels in 610 uniformly distribute the acquired fluids in a longitudinal direction of the absorbent pad 610 thereby increasing the absorption rate of the pad. As can be seen in FIG. 4, approximately 76% of absorbent pad 610 has come into contact with fluid (approximately 170 millimeters of a pad approximately 225 millimeters in length), whereas only approximately 50% (112 millimeters out of 223 millimeters) and 33% (78 millimeters out of 233 millimeters) of absorbent pads 620 and 630 have come into contact with fluid, respectively.

Figure 5:
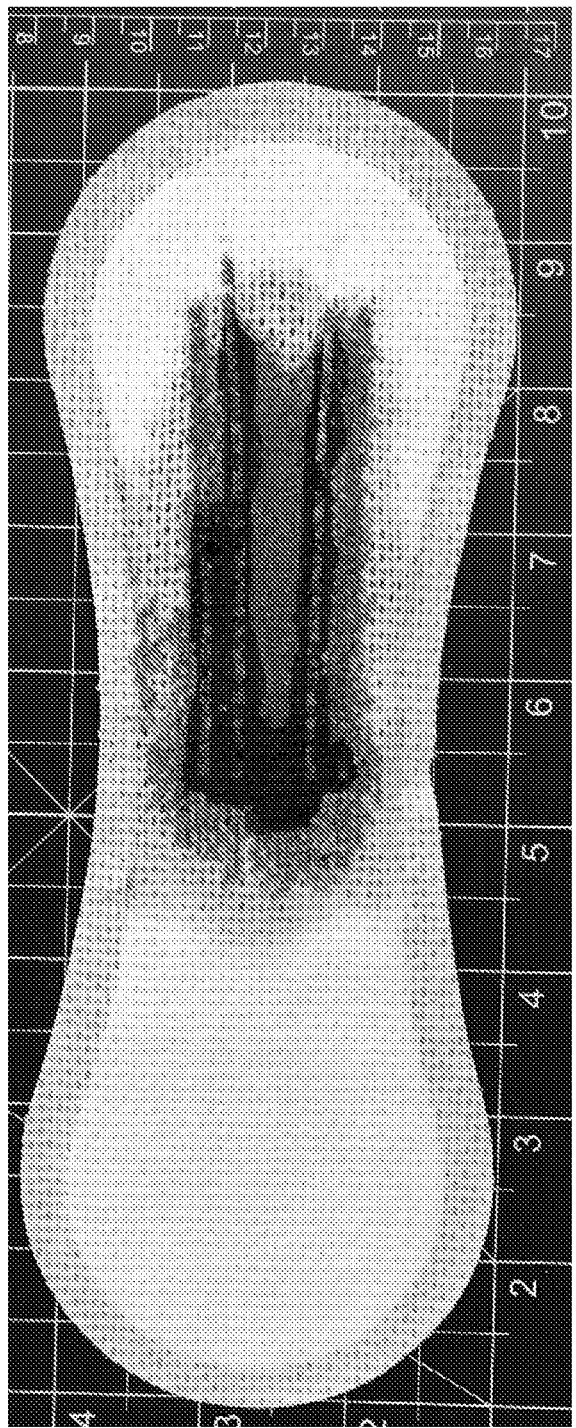
FIG. 5 shows an image of an exemplary ultrathin absorbent hygienic pad as disclosed herein having channels applied to only half of the pad, following application of fluid to the center (at 5.5 inches) of the ultrathin absorbent hygienic pad.
Figure 6A:
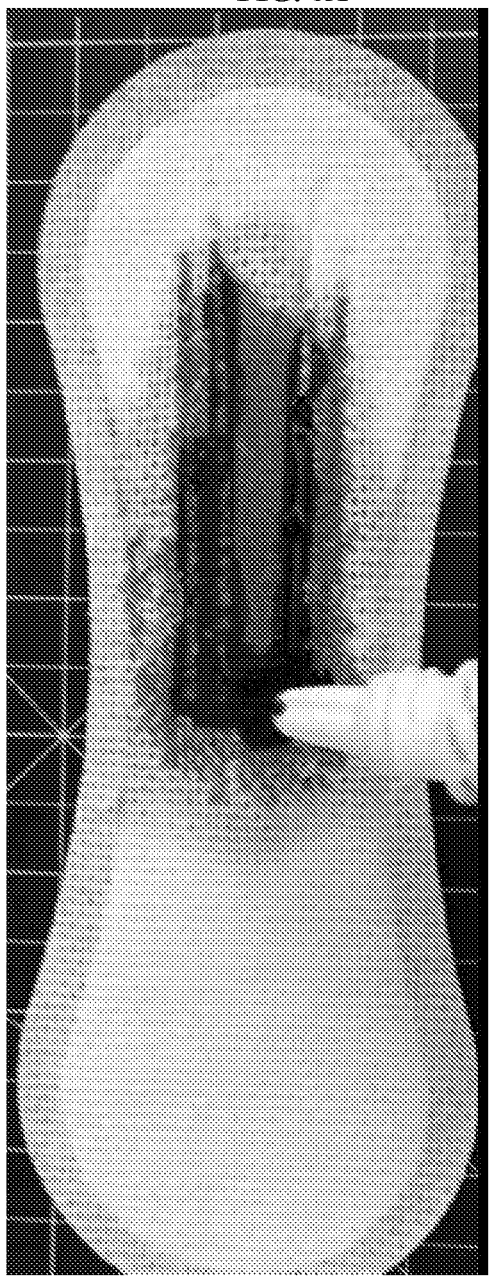
FIG. 6A-6D show a time-lapse of an exemplary ultrathin absorbent hygienic pad as disclosed herein having channels applied to only half of the pad.
Figure 6B:
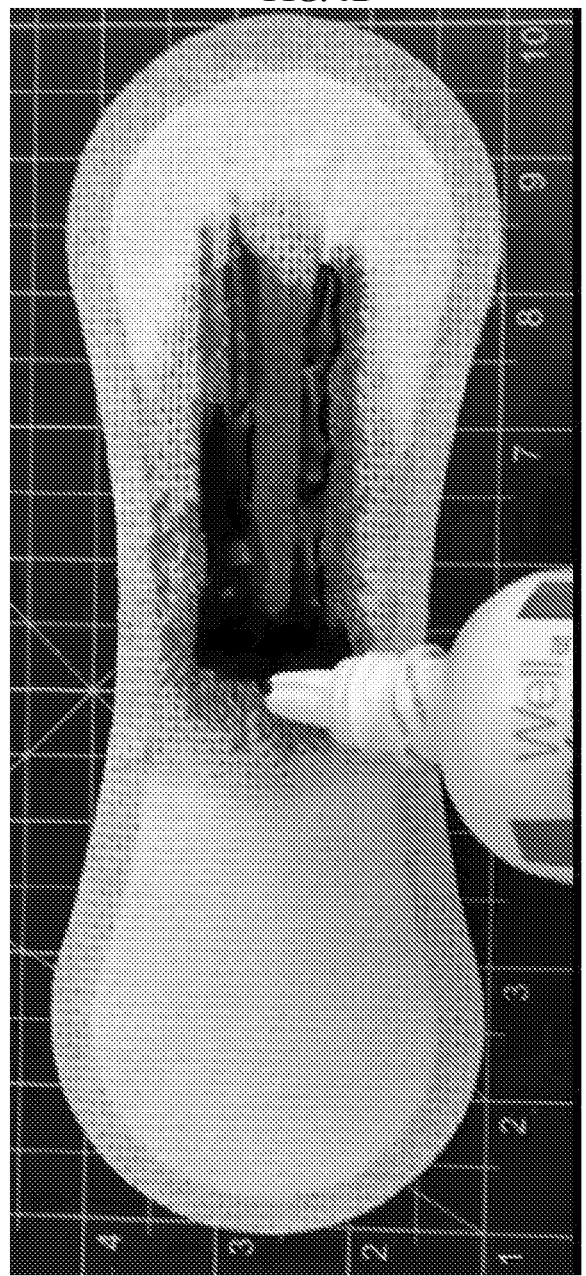
Figure 6C:
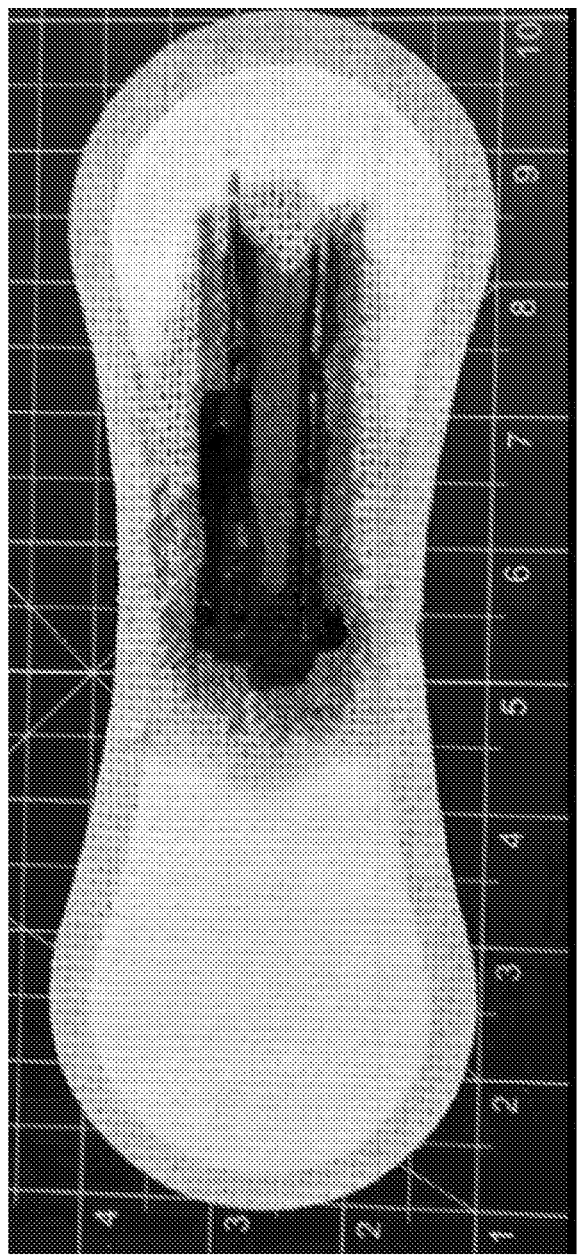
Figure 6D:
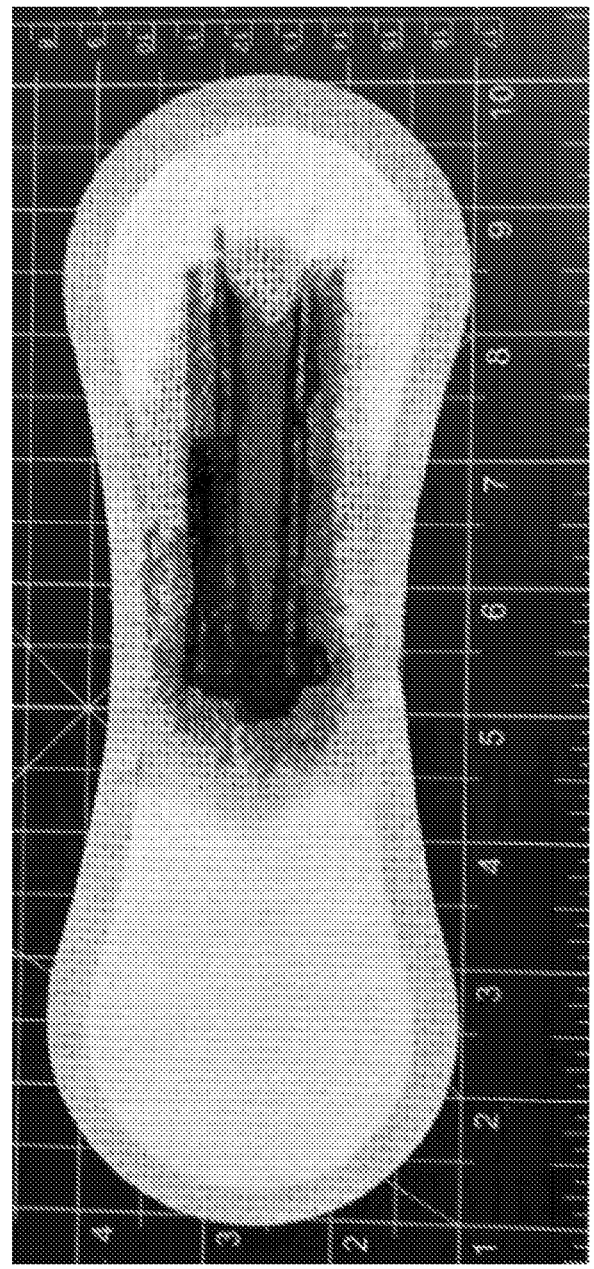
Figure 7A:
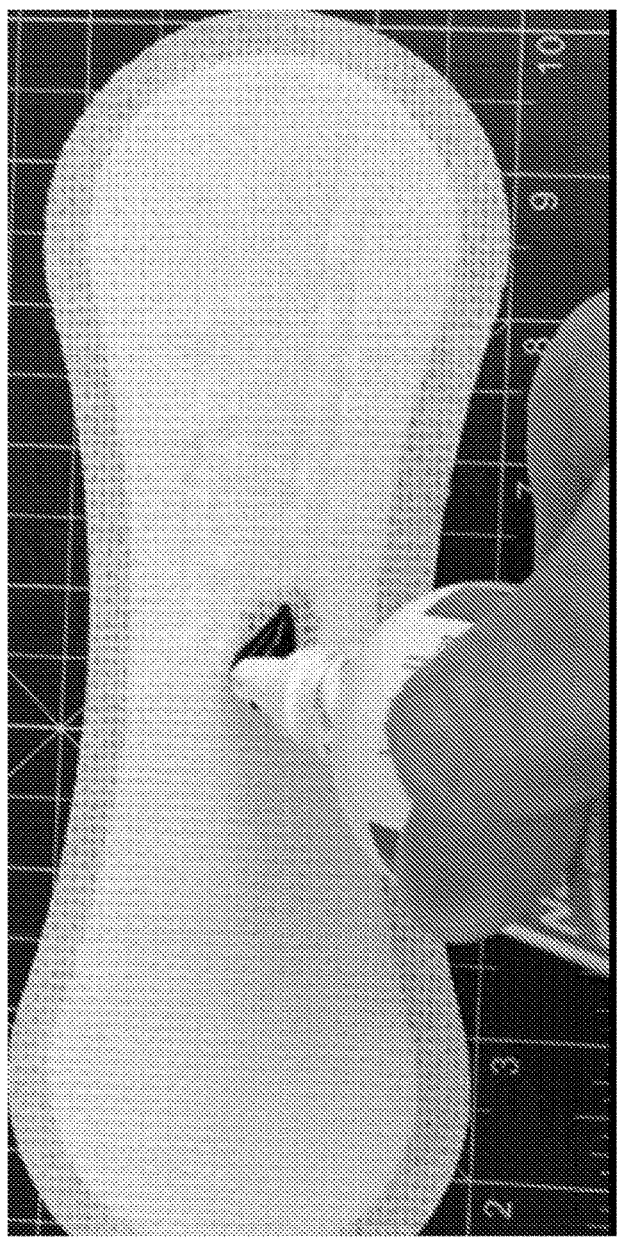
FIG. 7A-7D show a time-lapse of an exemplary ultrathin absorbent hygienic pad as disclosed herein having channels applied to only half of the pad.
Figure 7B:
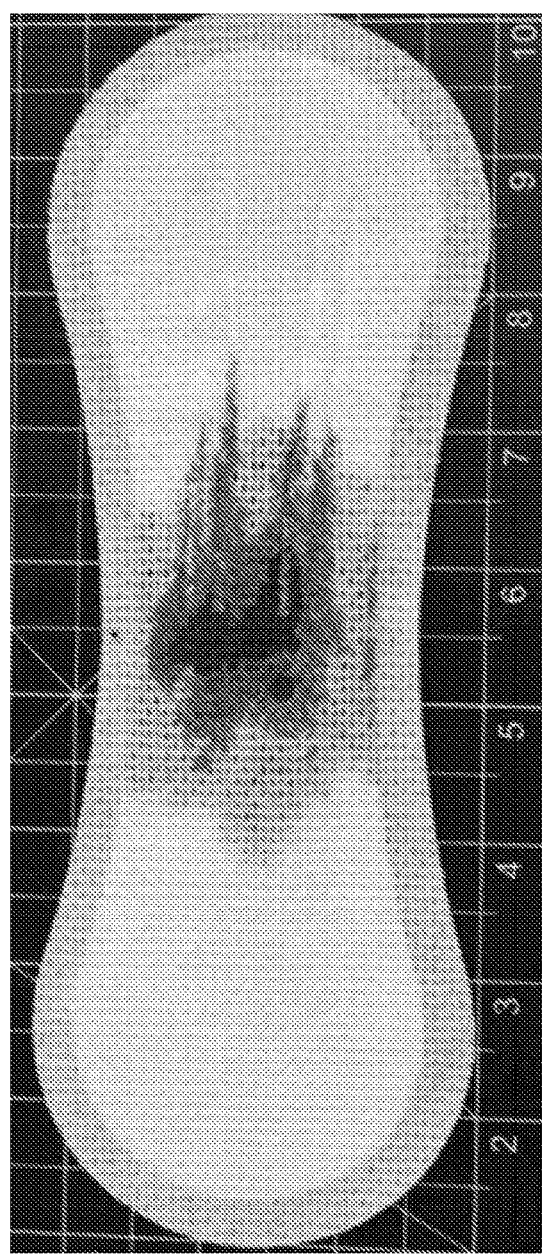
Figure 7C:
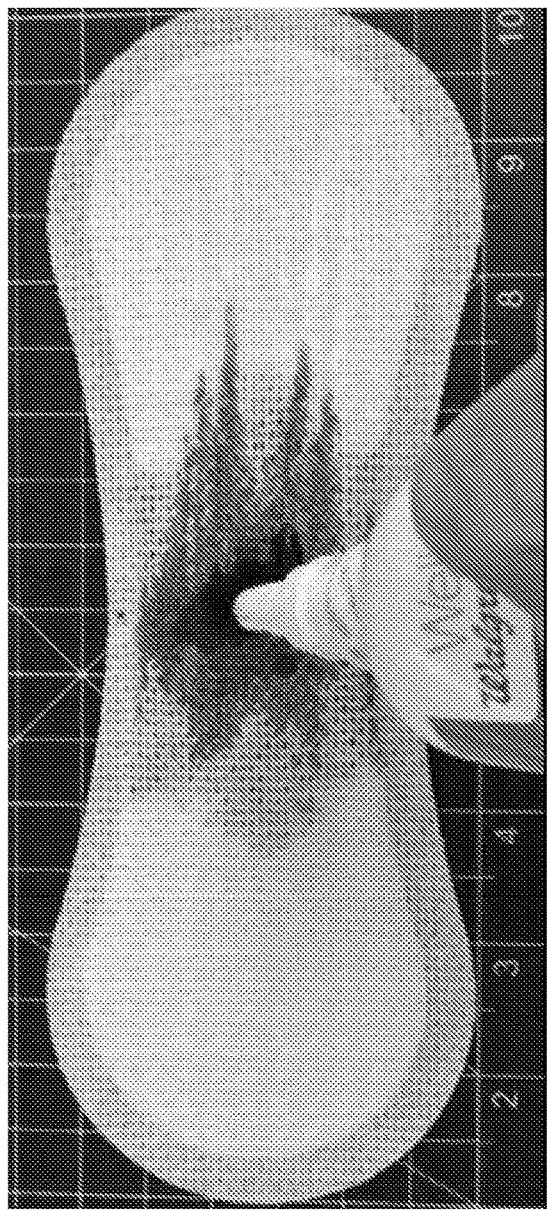
Figure 7D:

FIG. 5 illustrates an exemplary ultrathin absorbent hygienic pad as disclosed herein having channels applied to only half of the pad, where fluid has been applied to the center of the pad. Upon application of the fluid to the pad, the half of the pad with channels distributes liquid much more quickly and significantly into the entire pad and away from the point of insult (where fluid was applied, at the 5.5" mark at the center of the pad). The anchored channels allow the ultrathin absorbent hygienic pads disclosed herein to absorb more fluid as absorbent materials throughout the entire pad can be used, rather than just the absorbent materials situated at the point of insult, before leakage will occur off of the sides of the pad. FIG. 6 illustrates a time-lapse experiment involving an exemplary ultrathin absorbent hygienic pad as disclosed herein having channels applied to only half of the pad. FIG. 6A depicts application of fluid to an exemplary ultrathin absorbent hygienic pad, and FIGS. 6B, 6C, and 6D show images 7 seconds, 14 seconds, and 22 seconds after application, respectively. FIG. 7 illustrates a time-lapse experiment involving an exemplary ultrathin absorbent hygienic pad as disclosed herein having channels applied to only half of the pad. FIG. 7A depicts application of fluid to an exemplary ultrathin absorbent hygienic pad, and FIGS. 7B, 7C, and 7D show images 60 seconds, 90 seconds, and 170 seconds after application, respectively. Additional fluid was added during the course of the experiment, as can be seen in FIGS. 7C and 7D. As can be seen in both FIG. 6 and FIG. 7, the channels remain functionally intact even after application of fluid and swelling of the region immediately surrounding the channel. The channels effectively disperse the fluid along the length of the pad, maximizing the absorption of the fluid storage material and minimizing the possibility that fluid will leak off the sides of the pad next to where the fluid was applied.

Methods of Manufacturing

In some embodiments, provided herein are methods of manufacturing absorbent articles. Processes for assembling absorbent articles include joining the bottom layer and/or the top layer to the middle absorbent layer or to each other by a uniform continuous layer of adhesive, a patterned layer of adhesive, or an array of separate lines, spirals, or spots of adhesive. In some embodiments, the methods of manufacturing absorbent articles disclosed herein comprise forming a bottom layer, forming an absorbent layer, forming a top layer, and combining those layers into an absorbent article, and then forming one or more channels in the top layer wherein the channels are anchored through the middle absorbent layer and into the bottom layer.

In some embodiments, the absorbent articles disclosed herein comprise one or more layers manufactured by a method comprising needle punching, spunlacing, wet-laying, dry-laying, meltblowing, needle bonding, stitch-bonding, hydroentanglement, and felting. In some embodiments, the absorbent articles disclosed herein comprise an absorbent layer manufactured by a method comprising needle punching, spunlacing, wet-laying, dry-laying, meltblowing, needle bonding, stitch-bonding, hydroentanglement, and felting. In some embodiments, the middle absorbent layer is stitch bonded with strengthening fibers or yarns to provide additional strength to the middle absorbent layer such that it retains its structure when saturated with fluid. In some embodiments, the stitch-bonded structure affords higher absorbency or a degree of extensibility to the absorbent article depending on the nature of the strengthening fibers and yarns used and their stitch-bonding pattern. In some embodiments, the absorbent articles disclosed herein are formed by methods including adhesion, flame lamination and ultrasound.

EXAMPLES

Example 1

Comparison of fluid distribution and absorption. An ultrathin absorbent hygienic pad comprising one or more anchored channels (see, e.g., FIG. 2) is placed on a table with its top layer facing up. Two or more absorbent hygienic pads without one or more anchored channels are arranged in a similar manner next to the ultrathin absorbent hygienic pad comprising one or more anchored channels. Each pad has the same amount of fluid (for example, 45 milliliters) applied to the center of the pad. After approximately 2 minutes, the fluid distribution and absorption is determined for each of the pads. The ultrathin absorbent hygienic pad comprising one or more anchored channels has fluid in contact with significantly more area in the pad than the pads without one or more anchored channels. The pads lacking one or more anchored channels have absorbed fluid primarily at the center of the pad, close to where the fluid was applied, and have begun to show supersaturation of the fluid storage material at that region of the pad.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An absorbent article comprising: a top layer; a middle absorbent layer; and a bottom layer; wherein the top layer comprises one or more channels bonded to the top layer, the middle absorbent layer, and the bottom layer; wherein the top layer comprises a non-woven spun sheet bound to an aperture layer; wherein the middle absorbent layer comprises a fluid drawing material and a fluid storage material; wherein the one or more channels penetrate to a depth of no more than 50% of a thickness of the absorbent article: wherein the absorbent article has a thickness of no more than one millimeter.

2. The absorbent article of claim 1, wherein the one or more channels are bonded via ultrasonic welding from the top layer through the middle absorbent layer and into the bottom layer.

3. The absorbent article of claim 2, comprising two or more channels that are uniformly distributed across the absorbent article to absorbs fluids in a longitudinal direction of the absorbent article increasing the absorption rate of the pad wherein 76% of absorbent article has come into contact with fluid when 45 millimeters of fluid is applied to the absorbent article.

4. The absorbent article of claim 3, wherein the top layer and the middle absorbent layer are bonded together with an adhesive.

5. The absorbent article of claim 4, wherein the aperture layer comprises a plurality of holes.

6. The absorbent article of claim 1, wherein the fluid drawing material comprises electrospun nanofibers, which contain superabsorbent material packets throughout.

7. The absorbent article of claim 1, wherein the fluid storage material comprises superabsorbent polymer.

8. The absorbent article of claim 1, wherein the one or more channels are arranged such that a distance from a midline of the absorbent article to the one or more channels varies along a length of the one or more channels.

9. The absorbent article of claim 1, wherein the absorbent article has a thickness of no more than one millimeter.

10. The absorbent article of claim 1, wherein the bottom layer comprises an adhesive region on a side opposite to a side in contact with the middle absorbent layer.

11. The absorbent article of claim 10, wherein the adhesive region on a side opposite to a side in contact with the middle absorbent layer is in contact with the wrapper element.

12. The absorbent article of claim 11, wherein the absorbent article is folded such that the folded absorbent article is completely enclosed by the wrapper element.

13. The absorbent article of claim 1, wherein the absorbent article is a menstrual pad about 155 millimeters long and about 60 millimeters wide.

14. The absorbent article of claim 1, wherein the absorbent article is a menstrual pad about 305 millimeters long and about 85 millimeters wide.

15. The absorbent article of claim 1, wherein the absorbent article is a bladder liner about 200 millimeters long and about 90 millimeters wide at one end and 65 millimeters wide at an opposite end.

* * * * *